United States Patent [19]

Anderson

[11] Patent Number: 4,976,618
[45] Date of Patent: Dec. 11, 1990

[54] APPARATUS AND METHOD FOR TREATING TEMPOROMADIBULAR JOINT DYSFUNCTION AND BRUXISM

[76] Inventor: Kent Anderson, 4015 Creek View Ct., Rocklin, Calif. 95677

[21] Appl. No.: 358,868

[22] Filed: May 30, 1989

[51] Int. Cl.$^5$ ............................................. A61C 19/04
[52] U.S. Cl. ...................................... 433/215; 433/6; 433/72; 128/777
[58] Field of Search .................. 433/6, 68, 69, 215, 433/72

[56] References Cited

U.S. PATENT DOCUMENTS

| | | | |
|---|---|---|---|
| 2,311,158 | 2/1943 | Conway et al. | 433/37 |
| 3,349,489 | 10/1967 | Shackelford | 433/68 |
| 3,488,848 | 1/1970 | Lerman | 433/68 |
| 3,813,781 | 6/1974 | Forgione | 433/68 |
| 4,211,008 | 7/1980 | Lerman | 433/6 |
| 4,220,142 | 9/1980 | Rosen et al. | 128/1 R |
| 4,348,178 | 9/1982 | Kurz | 433/6 |
| 4,390,028 | 6/1983 | Okano et al. | 128/777 |
| 4,457,708 | 7/1984 | Dufour | 433/6 |
| 4,553,549 | 11/1985 | Pope et al. | 433/6 |
| 4,629,424 | 12/1986 | Lauks et al. | 433/6 |
| 4,669,477 | 6/1987 | Ober | 128/777 |
| 4,719,918 | 1/1988 | Bonomo et al. | 433/215 |
| 4,773,857 | 9/1988 | Herrin | 433/138 |
| 4,838,283 | 6/1989 | Lee, Jr. | 128/777 |
| 4,842,519 | 6/1989 | Dworkin | 128/777 |

Primary Examiner—John J. Wilson
Attorney, Agent, or Firm—Limbach, Limbach & Sutton

[57] ABSTRACT

The present invention provides an intraoral sensing device which generates a pressure change in cavities positioned between the upper and lower dental surfaces. This signal is used to provide a therapeutic apparatus and method for treatment of temporomandibular joint dysfunction and bruxism. An audible signal is generated to wake the patient from a nocturnal eqisode of abnormal jaw muscle activity. Control means are provided to establish a threshold value below which no audio signal is generated.

7 Claims, 2 Drawing Sheets

APPARATUS AND METHOD FOR TREATING TEMPOROMADIBULAR JOINT DYSFUNCTION AND BRUXISM

TECHNICAL FIELD

This invention relates generally to apparatus and methods which are useful in the diagnosis and treatment of stress-related temporomandibular dysfunction and bruxism. More specifically, this invention relates to an intraoral device which can detect abnormal jaw muscle activity associated with these conditions by a gas or fluid pressure change in a flexible channel positioned between the posterior occlusal portions of the mouth.

BACKGROUND OF THE INVENTION

The mandible is connected to the cranium by the temporomandibular joints, located immediately in front of the ears. Rotation of the mandible about these joints is accomplished by the masticatory muscles, each of which extends from an opposite side of the mandible to a connecting point on the cranial bones. The masticatory muscles have an at rest position between their extended and contracted states. Under normal physiological conditions involving the outgrowth of a full complement of teeth, the mandibular portion of each temporomandibular joint will rest lightly in the cranial portion of the joint, and the muscles will be relaxed, or at rest.

Masticatory muscle related stresses and/or pain can arise due to differences in occlusal pressures along the upper and lower dental arches. Temporomandibular joint dysfunction syndrome relates to occlusion-muscle incompatibility. Masticatory muscle accommodation is a key factor in the etiology of this syndrome. Psychological tension and stress can lead to temporomandibular joint dysfunction or bruxism in otherwise stable mouths with normal occlusion.

The most frequent jaw movement involves elevation of the mandible from its rest position into centric occlusion. Simple elevation of the mandible is normally powered almost entirely by the elevator muscles, other muscles providing only a minor bracing action. The bilateral temporals, masseters and medial pterygoids provide an excess supply of elevator motor units. Since these motor units alternate in function, with fatigued units "dropping out" to rest while others take their place, mandible elevation can be continued almost indefinitely without overfatiguing these muscles.

Occlusion-muscle dysfunction alters this condition drastically because accommodation has a highly selective effect on the masticatory muscles, increasing their activity disproportionately in certain areas of the bilateral complex. In the presence of occlusionmuscle disharmony, atraumatic closure into centric occlusion requires that the mandible be adjusted every time it is elevated into occlusion. If, for example, the required adjustment is horizontal, the muscle areas capable of producing such horizontal movements must be called into activity with the same frequency as are the elevator muscle areas Unfortunately, there are far fewer of these horizontal-adjustor motor units than elevator motor units.

Ultimately the functional capacity of these comparatively few horizontal motor units is exceeded, which triggers an exhaustion-incoordination-spasm sequence and development of the temporomandibular joint syndrome symptoms The resulting tenderness and spasm are found most frequently in the lateral pterygoid muscles which function as anterior adjustors of mandibular placement.

In psychological stress related syndromes, the muscles become fatigued as a result of nocturnal clenching or grinding of the teeth. These nocturnal activities give rise to the same symptoms as malocclusion-based temporomandibular joint dysfunction.

The sequence of muscle dysfunction spreads beyond the masticatory muscles, producing an entire constellation of primary symptoms of the temporomandibular joint pain-dysfunction syndrome. These symptoms include pain and/or tenderness in the temporomandibular joint area or masticatory muscles; "clicking" in the temporomandibular joint; limitation of jaw opening; restriction of jaw movement; and secondary symptoms which are medical in nature, being transmitted to other, more distant areas of the head and neck. These secondary symptoms probably include some of the most widespread and problematic conditions medicine has to deal with, namely, headache (including "tension" headaches, which account for 90% of all headache), atypical facial neuralgias, tinnitus, and neck and ear pain, among others. Also, certain neuromuscular disorders of the face, head and neck, shoulders, back, arms and hands can occur. These secondary symptoms are functional disturbances which exhibit no organic changes in the affected tissues, making diagnosis difficult. They are often ill-defined and difficult for the patient to describe.

These symptoms are usually diagnosed as purely medical in nature because they occur at some distance from the teeth. Their masticatory muscle origin unfortunately is not readily apparent. The usual result is that treatment is mistakenly directed to the secondary symptom's locale rather than to the underlying "invisible malocclusion." Such invisible malocclusions are common, but difficult to detect. Intercuspation of the teeth appears normal, while the underlying faulty (accommodation-necessitating) craniomandibular relationship is hidden by the automatic compensatory action of the muscles. The secondary symptoms resulting from temporomandibular joint dysfunction thus are usually treated palliatively instead of having their basic cause eliminated. For malocclusion-based muscle dysfunction definitive therapy is essentially an orthopedic procedure and requires correction of the faulty cranio-mandibular relationship by a dentist. For psychological-stress related dysfunctions, orthopedic procedures are largely unnecessary. In these cases, negative psychological feedback, such as described hereinafter, can be used to interrupt the stress-related grinding or clenching events.

A related condition is known as bruxism. This condition involves abnormal and excessive grinding of the teeth, typically during sleep. This condition has been linked to episodes of emotional stress. Excessive grinding, if unchecked, can lead to malocclusion and result in the occurrence of malocclusion-related temporomandibular joint dysfunction syndrome described above.

Prior art methods of treating temporomandibular joint dysfunction and bruxism involve clinical monitoring devices to measure the amount of pressure being asserted, splints to be worn during sleep to prevent the wearing of teeth, and behavior modification devices wherein an electrical shock is provided to the jaw muscles to interrupt a nocturnal episode without waking the patient. The present invention provides for the first time an intraoral sensing device and therapeutic apparatus which does not require continual clinical monitoring. It is relatively low cost and very simple to use.

SUMMARY OF THE INVENTION

The present invention provides a novel intraoral sensing device which is horseshoe-shaped, and in its preferred embodiment, designed to be received by the upper arch of the mouth. At the open ends of the horseshoe shape are right and left posterior occlusal portions which are to be received between the upper and lower dental arches. These occlusal portions contain an elongate flexible cavity whose longitudinal axis runs horizontally, from posterior to anterior regions of the mouth. The cavity is air-tight, fluid-sealed at its posterior end, but gas and fluid communicating at its anterior end. Adjacent to these posterior occlusal portions are buccal engagement means which assist in the stability of the device in the mouth. The horseshoe shape is completed by a frenum-receiving labial portion.

According to the present invention, this intraoral sensing device is used in combination with a fluid tube which connects the sensing device to signal receiving means, signal generating means and control means to activate the signal generating means when the received signal value exceeds a preset value. The connection of the flexible tube to the signal receiving means enables the detection of gas or fluid pressure changes in the flexible cavity caused by abnormal, nocturnal jaw muscle activity. When this activity exceeds a preset level, control means activates the signal generating means to create a signal which will wake the user from the nocturnal episode. This continued interruption of sleep will lead to appropriate behavior modification to eliminate bruxism or clenching.

It is therefore an object of this invention to provide a therapeutic apparatus for use in treating temporomandibular joint dysfunction and bruxism which is relatively inexpensive.

It is a further object of this invention to provide a therapeutic apparatus and method which is easy to use.

It is an object of this invention to provide a therapeutic apparatus which does not have to be used with direct and frequent clinical supervision.

It is also an object of this invention to provide a dental appliance which does not have to be molded or cast for each individual patient.

It is an object of this invention to provide an apparatus and method which is useful in diagnosis and evaluation of the temporomandibular joint dysfunction to assist in evaluating whether the dysfunction was caused by malocclusion or psychological stress.

These and further objects of the present invention will become apparent to those of ordinary skill in the art from the following specifications and figures.

DETAILED DESCRIPTION OF THE INVENTION

Figure 1:
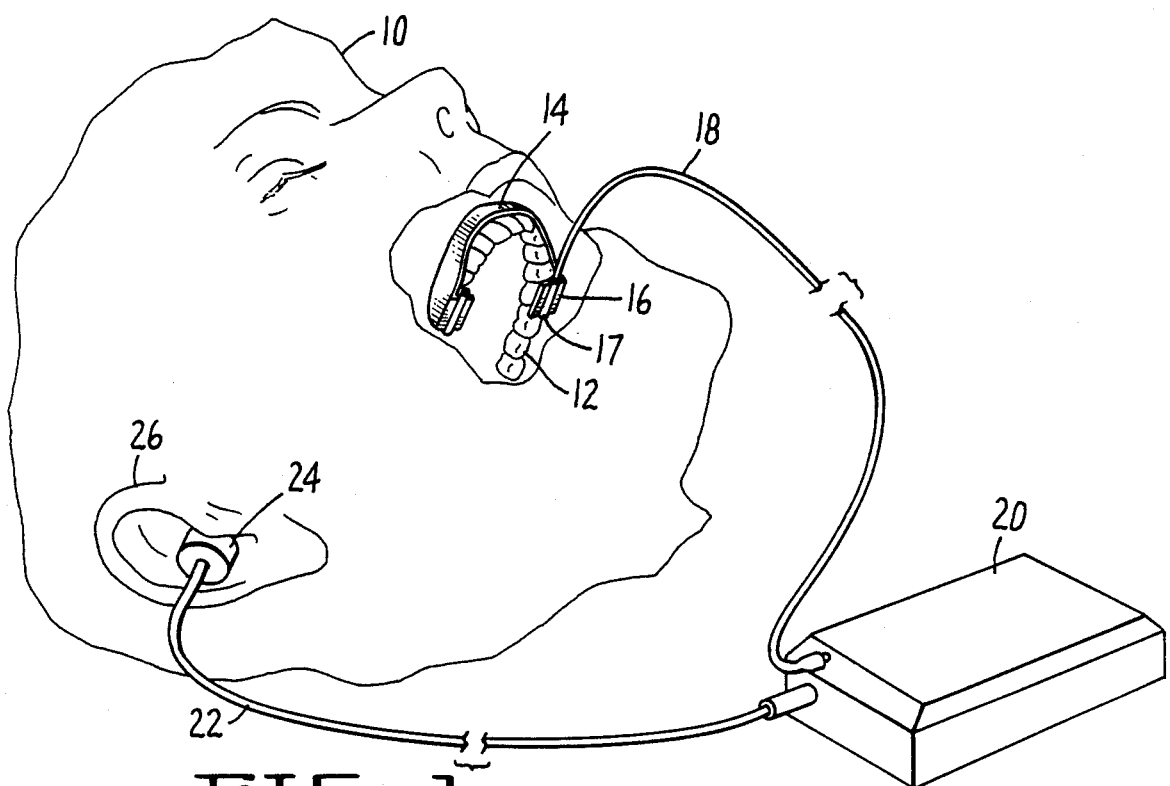
FIG. 1 is a perspective view of the preferred embodiment of the therapeutic apparatus according to the instant invention, worn on the patient's upper dental arch.

Referring to FIG. 1 there is seen a patient 10 wearing the therapeutic apparatus of the instant invention. The patient's upper dental arch 12 is received within an intraoral sensing device 14. A posterior occlusal portion 16 of the device 14 contains a flexible cavity 17. The posterior end of the flexible cavity 17 is sealed off, but the anterior end of flexible cavity 17 connects and communicates with a fluid tube 18. Fluid tube 18 is connected at its other end to a signal receiver/signal generator 20. In this embodiment, an earphone lead wire is connected at one end to the signal receiver/signal generator 20, and at the other to an earphone 24 received in the patient's ear 26.

Figure 2:
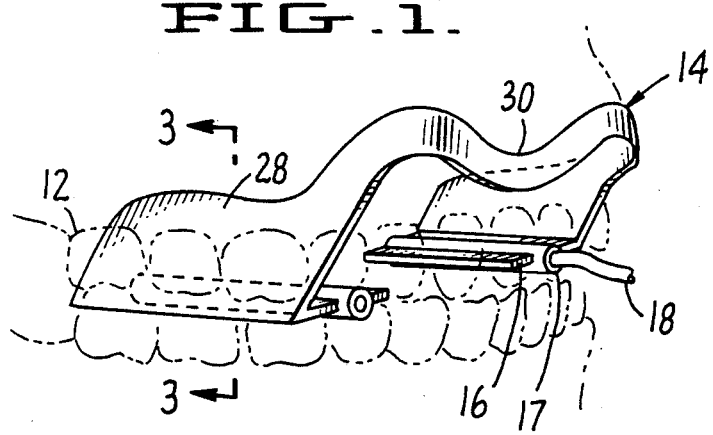
FIG. 2 is a perspective view of the upper and lower dental arches and intraoral sensing device, partially broken away to detail the intraoral sensing device.
Figure 3:
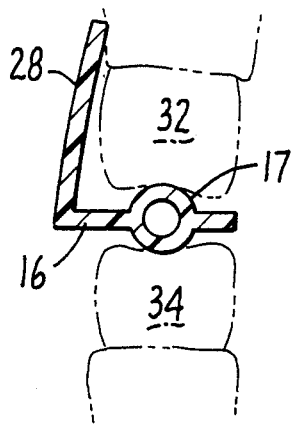
FIG. 3 is a cross sectional view of the flexible cavity, taken along the line 3—3 in FIG. 2.

Before discussing the interaction between the patient and the therapeutic apparatus, it is first necessary to describe the components of the intraoral sensing device 14. As seen in FIGS. 2 and 3, this horseshoe-shaped appliance fits onto the upper dental arch 12. While the upper dental arch is the preferred embodiment, it is clearly within the scope of the invention, and claims appended hereto, to fit the appliance on the lower dental arch. The posterior occlusal portion 16 is positioned on a horizontal plane between the upper and lower dental arches. In this position, the posterior occlusal portion 16 is acted upon by the occlusal surfaces of the upper and lower dental arches. A flexible cavity 17 is contained within the posterior occlusal portion 16. Cavity 17 is sealed off at its posterior end. This cavity 17 serves as a sensing device because it contains a fixed volume of gas or fluid. When the posterior occlusal portion 16 is compressed by action of the grinding or clenching teeth 32 and 34 in the upper and lower dental arches, there is a change in the volume of the flexible cavity 17, and a corresponding change in the pressure ($PV = nRT$) of the gas or fluid contained within the cavity 17. This pressure change in cavity 17 can be detected and used as an indication of abnormal jaw muscle activity.

The intraoral sensing device 14 has additional features which insure its stability during nocturnal wear. A buccal engagement portion 28 is provided adjacent to the posterior occlusal portion 16. A second buccal engagement portion is provided on the other side of the horseshoe-shaped appliance, but it is not easily seen in the views presented. The buccal engagement portion 28 helps to keep the appliance 14 in place. At the anterior portion of the appliance 14 there is a labial, frenum-receiving portion 30. Portion 30 serves to keep both occlusal portions together, and its arcuate shape makes it more comfortable to wear.

Figure 4:
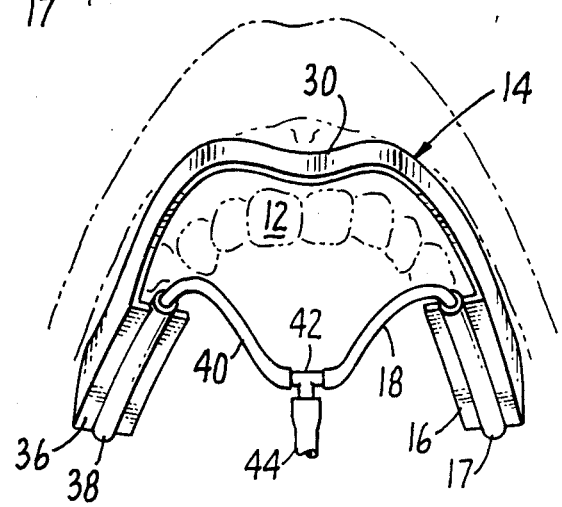
FIG. 4 is a perspective view of an alternate embodiment of the intraoral and therapeutic device of the present invention.

An alternate embodiment of the present invention is shown in FIG. 4. In this embodiment, a pressure change signal is detected in both posterior occlusal portions. The intraoral device 14 is the same as used in the above described preferred embodiment. It is received by the patient's upper dental arch 12, this view serving to further illustrate how the arcuate labial portion 30 is adapted to receive the patient's frenum. On the right side of the appliance 14 is a posterior occlusal portion 16 containing a flexible cavity 17 which is connected to fluid tube 18. On the left side, posterior occlusal portion 36 contains a flexible cavity 38 which is connected to a fluid tube 40. Fluid tubes 18 and 40 are connected to tee junction 42, and a signal tube 44 leads away from the tee junction 44 to the signal receiver (not shown in this figure.)

The intraoral sensing device 14 must be suitably flexible, at least in the posterior occlusal portions, to respond to jaw muscle activity. This flexibility is achieved by the use of rubber-like materials such as polyvinyl chloride, polyurethane, polybutylene, polyethylene and thermoplastics, generally. The device 14 is easily injection-molded, although care must be taken to prevent inadvertent closure of the flexible cavities 17 and 38. While in the preferred embodiment, cavities 17 and 38 have circular cross-sections, it is possible to use other geometric shapes to achieve the same result. It is also contemplated that the flexible cavity can act as a manifold, connecting with a series of fluid tubes which can be used to detect regional pressure changes.

The preferred embodiment of the present invention has been described with reference to the use of air as the gas contained within the flexible cavity and fluid tube. It should be well understood that fluids such as water and mineral oil may be used with this device to achieve substantially the same result.

The method of the instant invention relates to the therapeutic use of the above described apparatus. The patient first installs the intraoral sensing device 14 on his upper dental arch 12. The flexible cavity 17 is connected to the fluid tube 18 which is in turn connected to the signal receiving means contained within the black plastic device 20. The patient can then set the control means at a level truly indicative of abnormal, nocturnal jaw activity. This is accomplished by trial and error, with the patient intentionally moving his jaw to trigger an audible signal. The black plastic device 20 is provided with a control means which will not activate the audible signal generating means unless the jaw muscle activity exceeds the preset threshold. Thus, when the patient 10 wears the therapeutic apparatus to bed, he must install the earplug 24 within his ear 26.

The therapeutic aspect of this method involves the use of negative feedback. Once the intraoral sensing device is installed, and an abnormal jaw muscle event occurs nocturnally, then the signal receiving means receives a pressure change signal from the intraoral sensing device 14. This pressure change signal is quantified and its value compared with the preset control threshold value. If the measured signal is not in excess of the preset threshold, then the control means does not activate the audible signal generating means. If the measured signal exceeds the preset threshold value, then the control means activates the audible signal generating means which then generates an audible signal to be transmitted through the earphone lead wire 22 into the earphone 24. The audible tone in the earphone 24 then wakes the patient, ending the nocturnal episode of bruxism, or other abnormal jaw activity.

Figure 5:
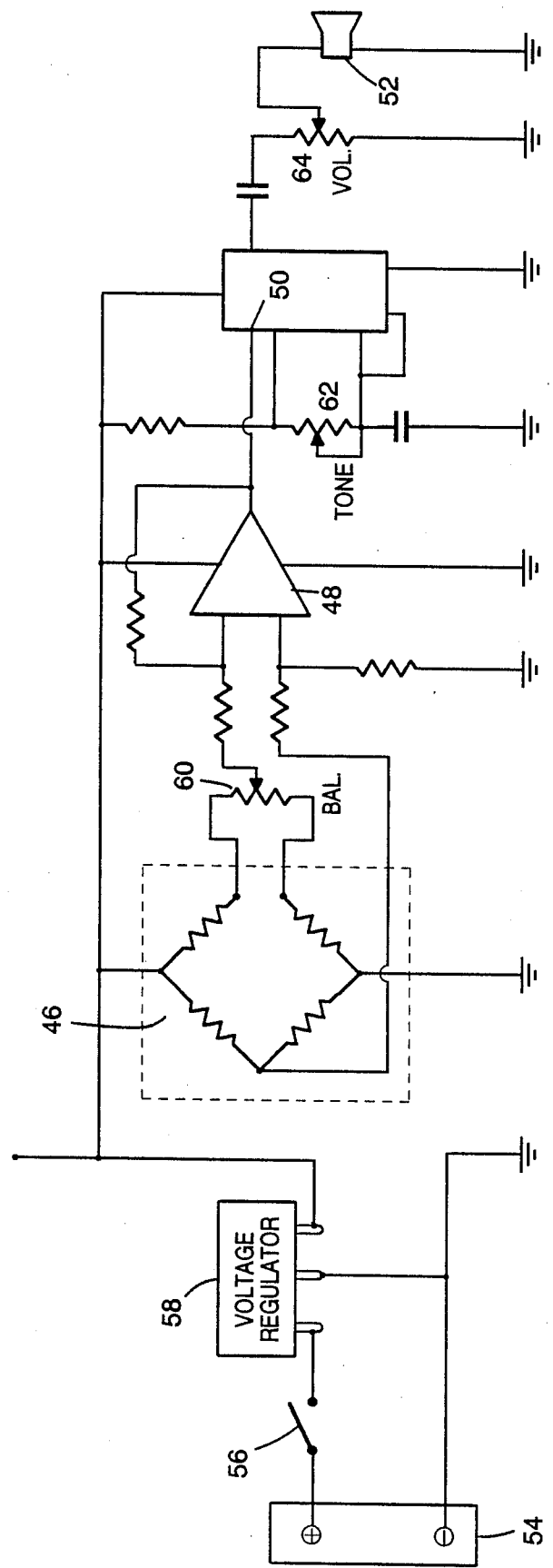
FIG. 5 is a schematic diagram of the signal receiving means, signal generating means and control means according to the instant invention.

A preferred embodiment of the circuitry for the signal receiving means, signal generating means and control means for comparing the measured signal to a preset value and for activating the signal generating means is shown in the schematic diagram of FIG. 5.

Pressure on the intraoral sensing device increases the air pressure in a tube connected to the input of the pressure transducer, 46. This causes an imbalance of voltage across the resistive bridge circuit and the difference voltage is amplified by an operational amplifier, 48. The amplified voltage is applied to pin 4 of 50, a type 555 timer connected as an audio oscillator circuit. When the voltage at pin 4 (50) exceeds +0.7 volts, the oscillator circuit is turned "ON" producing an audible frequency output in the earphone, 52. When pressure on the intraoral sensing device is removed, the imbalance of voltage across the bridge circuit of 46 is removed, the voltage applied to pin 4 of 50 drops below +0.7 volts and the oscillator voltage output drops to zero.

The circuit voltage is obtained from a single 9 volt battery, 54 with an ON/OFF switch, 56. A voltage regulator 58 maintains a 5.0 volt source for the circuit. A momentary switch, SW2 in series with a zener diode a resistor and an LED enable a test of the battery charge condition. If the LED light is dim or off when the switch, SW2 is depressed, the battery should be replaced This part of the circuit is not shown in FIG. 5.

Three potentiometers are used to enable adjustment on the unit. The BALANCE control 60, enables adjustment for a zero audible output when no pressure is applied to the mouthpiece. The TONE control, 62, permits the adjustment of the audible signal to the frequency preferred by the user. The VOLUME control, 64, permits an adjustment of the output to the level preferred by the user.

While the instant invention has been described with reference to particularly preferred embodiments, it will be apparent to those of ordinary skill in the art that modifications may be made which fall within the scope of the claims appended hereto.

What is claimed is:

1. An intraoral sensing device, adapted for placement in the upper arch of the human mouth, for generating a detectable signal indicative of jaw muscle activity associated with nocturnal episodes of temporomandibular joint dysfunction or of bruxism, which comprises:

a flexible, unitary horseshoe-shaped appliance adapted to be received within the upper arch of the human mouth, said appliance having right and left posterior occlusal portions, which portions are adapted to be received between occlusal surfaces of the upper and lower dental arches, at least one of said posterior occlusal portions containing a separate elongate, flexible cavity whose longitudinal axis runs in a generally horizontal direction from the posterior to anterior regions of the human mouth, said elongate, flexible cavity sealed at its posterior end and open at its anterior end, said flexible cavity capable of containing a preselected volume of fluid or gas at a preselected pressure, so that a detectable pressure change is obtained when said flexible cavity volume is decreased by jaw muscle activity in response to an episode of temporomandibular joint dysfunction or of buxism, said horseshoe-shaped appliance also having an arcuate, frenum-receiving labial portion which connects the two posterior occlusal portions to obtain said horseshoe shape, and also having buccal engaging means along an outer edge of said posterior occlusal portions to maintain said occlusal portions between the posterior teeth of the upper and lower dental arches.

2. The intraoral sensing device of claim 1 wherein both posterior occlusal portions contain separate elongate, flexible cavities.

3. A therapeutic apparatus for the treatment of nocturnal episodes of temporomandibular dysfunction of a bruxism which comprises:

an intraoral sensing device comprising a flexible, unitary horseshoe-shaped appliance adapted to be received within the upper arch of the human mouth, said appliance having right and left posterior occlusal portions, adapted to be received between the occlusal surfaces of the upper and lower dental arches, at least one of said posterior occlusal positions containing a separate elongate, flexible cavity whose longitudinal axis runs in a generally horizontal direction from the posterior to anterior regions of the human mouth, said elongate, flexible cavity sealed at its posterior end and open at its anterior end, said horseshoe-shaped appliance also having an arcuate, frenum-receiving labial portion which interconnects the two posterior occlusal portions to obtain said horseshoe shape, and also having buccal engaging means along an outer edge of said posterior occlusal portions to help maintain said occlusal portions between the posterior teeth of the upper and lower dental arches;

signal receiving means capable of detecting and quantifying a fluid pressure signal;

signal generating means for producing an audible signal responsive to control means;

control means for comparing a fluid pressure signal detected and quantified by said signal receiving means with a preset fluid pressure value and for activating said signal generating means when said detected fluid pressure signal exceeds said preset fluid pressure value; and a fluid tube connected at one end to said occlusal portion elongate, flexible cavity anterior end and said fluid tube connected at its other end to said signal receiving means wherein said intraoral sensing device generates a fluid pressure signal in response to a nocturnal episode of temporomandibular joint dysfunction or a bruxism which pressure change signal is received and quantified by said signal receiving means and then compared to a predetermined value by said control means, whereby an audible signal is produced in the event said fluid pressure signal exceeds the predetermined value, said audible signal wakes the patient to end the nocturnal episode.

4. The therapeutic apparatus of claim 3 wherein both posterior occlusal portions of said intraoral sensing device contain separate elongate, flexible cavities.

5. An intraoral sensing device, adapted for placement in the lower arch of the human mouth, for generating a detectable signal indicative of jaw muscle activity associated with nocturnal episodes of temporomandibular joint dysfunction or of buxism, which comprises:

a flexible, unitary horseshoe-shaped appliance adapted to be received within the lower arch of the human mouth, said appliance having right and left posterior occlusal portions, which portions are adapted to be received between occlusal surfaces of the upper and lower dental arches, at least one of said posterior occlusal portions containing a separate elongate, flexible cavity whose longitudinal axis runs in a generally horizontal direction from the posterior to anterior regions of the human mouth, said elongate, flexible cavity sealed at its posterior end and open at its anterior end, said flexible cavity capable of containing a preselected volume of fluid or gas at a preselected pressure, so that a detectable pressure change is obtained when said flexible cavity volume is decreased by jaw muscle activity in response to an episode of temporomandibular dysfunction or of bruxism, said horseshoe-shaped appliance also having an arcuate labial portion which connects the two posterior occlusal portions to obtain said horseshoe shape, and also having buccal engaging means along an outer edge of said posterior occlusal portions to maintain said occlusal portions between the posterior teeth of the upper and lower dental arches.

6. A therapeutic apparatus for the treatment of nocturnal episodes of temporomandibular dysfunction of a bruxism which comprises:

an intraoral sensing device comprising a flexible, unitary horseshoe-shaped appliance adapted to be received within the lower arch of the human mouth, said appliance having right and left posterior occlusal portions, adapted to be received between the occlusal surfaces of the upper and lower dental arches, at least one of said posterior occlusal positions containing a separate elongate, flexible cavity whose longitudinal axis runs in a generally horizontal direction from the posterior to anterior regions of the human mouth, said elongate, flexible cavity sealed at its posterior end and open at its anterior end, said horseshoe-shaped appliance also having an arcuate labial portion which interconnects the two posterior occlusal portions to obtain said horseshoe shape, and also having buccal engaging means along an outer edge of said posterior occlusal portions to help maintain said occlusal portions between the posterior teeth of the upper and lower dental arches;

signal receiving means capable of detecting and quantifying a fluid pressure signal;

signal generating means for producing an audible signal responsive to control means;

control means for comparing a fluid pressure signal detected and quantified by said signal receiving means with a preset fluid pressure value and for activating said signal generating means when said detected fluid pressure signal exceeds said preset fluid pressure value; and a fluid tube connected at one end to said occlusal portion elongate, flexible cavity anterior end and said fluid tube connected at its other end to said signal receiving means wherein said intraoral sensing device generates a fluid pressure signal in response to a nocturnal episode of temporomandibular joint dysfunction or a bruxism which pressure change signal is received and quantified by said signal receiving means and then compared to a predetermined value by said control means, whereby an audible signal is produced in the event said fluid pressure signal exceeds the predetermined value, said audible signal wakes the patient to end the nocturnal episode.

7. A method for the treatment of nocturnal episodes of temporomandibular joint dysfunction or of bruxism which comprises the steps of:

a. providing a therapeutic apparatus including: an intraoral sensing device comprising a flexible, unitary horseshoe-shaped appliance adapted to be received within the lower arch of the human mouth, said appliance having right and left posterior occlusal portions, adapted to be received between the occlusal surfaces of the upper and lower dental arches, at least one of said posterior occlusal portions containing a separate elongate, flexible cavity whose longitudinal axis runs in a generally horizontal direction from the posterior to anterior regions of the human mouth, said elongate, flexible cavity sealed at its posterior end and open at its anterior end, said horseshoe-shaped appliance also having an arcuate labial portion which interconnects the two posterior occlusal portions to obtain said horseshoe shape, and also having buccal engaging means along an outer edge of said posterior occlusal portions to help maintain said occlusal portions between the posterior teeth of the upper and lower dental arches;

signal receiving means capable of detecting and quantifying a fluid pressure signal;

signal generating means for producing an audible signal responsive to control means;

control means for comparing a fluid pressure signal detected and quantified by said signal receiving means with a preset fluid pressure value and for activating said signal generating means when said detected fluid pressure signal exceeds said preset fluid pressure value; and a fluid tube connected at one end to said occlusal portion elongate, flexible cavity anterior end and said fluid tube connected at its other end to said signal receiving means;

b. determining a minimum, threshold level of jaw muscle activity which is not truly related to an episode of temporomandibular joint dysfunction or of bruxism, and setting that level in said therapeutic apparatus control means, such that below said level said control means does not activate said signal generating means;

c. placing the intraoral sensing device and fluid tube of said assembled therapeutic apparatus in a patient's mouth; and d. wearing said intraoral sensing device during sleep, whereby said audible signal generating means is activated when abnormal jaw muscle activity exceeds said minimum, threshold level, waking the patient and ending the nocturnal episode of temporomandibular joint dysfunction or of bruxism.

* * * * *